(12) United States Patent
Wagshul et al.

(10) Patent No.: US 6,501,978 B2
(45) Date of Patent: Dec. 31, 2002

(54) INTERLEAVED OPERATION OF MRI AND ELECTRONIC EQUIPMENT

(75) Inventors: Mark Wagshul, Patchogue, NY (US); Todd Fjield, Shoreland, NY (US)

(73) Assignee: Transurgical, Inc., Setauket, NY (US)

( * ) Notice: Subject to any disclaimer, the term of this patent is extended or adjusted under 35 U.S.C. 154(b) by 214 days.

(21) Appl. No.: 09/752,603

(22) Filed: Dec. 29, 2000

(65) Prior Publication Data

US 2001/0049474 A1 Dec. 6, 2001

Related U.S. Application Data

(60) Provisional application No. 60/173,992, filed on Dec. 30, 1999.

(51) Int. Cl.$^7$ ............................................... A61B 5/055
(52) U.S. Cl. ........................ 600/411; 600/410; 600/427
(58) Field of Search ............................... 600/411, 410, 600/421, 417, 418, 427, 429, 430, 544, 9, 10

(56) References Cited

U.S. PATENT DOCUMENTS

| | | | |
|---|---|---|---|
| 5,357,958 A | * | 10/1994 | Kaufman .................... 600/410 |
| 5,485,839 A | | 1/1996 | Aida et al. ................ 128/653.1 |
| 5,841,278 A | | 11/1998 | Green et al. ................ 324/318 |
| 5,842,980 A | | 12/1998 | Tsuda ......................... 600/410 |
| 5,897,495 A | | 4/1999 | Aida et al. .................. 600/411 |
| 6,430,430 B1 | * | 8/2002 | Gosche ........................ 600/410 |
| 2001/0019306 A1 | * | 9/2001 | Tezuka ..................... 340/573.1 |
| 2002/0013612 A1 | * | 1/2002 | Whitehurst .................. 607/45 |

FOREIGN PATENT DOCUMENTS

| | | | | |
|---|---|---|---|---|
| JP | 8-140959 A | * | 6/1996 | ........... A61B/5/055 |
| WO | WO 98/52465 | | 11/1998 | |

* cited by examiner

*Primary Examiner*—Hieu T. Vo
(74) *Attorney, Agent, or Firm*—Lerner, David, Littenberg, Krumholz & Mentlik, LLP (57) ABSTRACT

An electrical appliance such as an ultrasonic energy applicator used in conjunction with magnetic resonance apparatus is controlled so that the appliance is active only while the magnetic resonance signals from the subject are not being received. Alternatively, magnetic resonance signals received while the appliance is operating can be rejected and the magnetic resonance cycles used to acquire such signals can be repeated. RF noise from the appliance does not affect the signals which are accepted and used to form an image.

26 Claims, 4 Drawing Sheets

INTERLEAVED OPERATION OF MRI AND ELECTRONIC EQUIPMENT

CROSS-REFERENCE TO RELATED APPLICATIONS

The present application claims the benefit of United States Provisional Application No. 60/173,992 filed Dec. 30, 1999, the disclosure of which is hereby incorporated herein.

FIELD OF THE INVENTION

The present invention relates to apparatus and methods employing magnetic resonance apparatus in conjunction with other electrical appliances.

BACKGROUND OF THE INVENTION

Copending, commonly assigned PCT International Publication WO98/52465, the disclosure of which is hereby incorporated by reference herein, describes an apparatus that incorporates magnetic resonance imaging capability in a relatively small device. Apparatus according to preferred embodiments disclosed in the '465 publication includes a movable static field magnet adapted to apply a static magnetic field in a magnetic resonance volume at a predetermined disposition relative to the static field magnet, and may also include an energy applicator such as a high intensity focused ultrasound or "HIFU" device. The preferred apparatus, according to the '465 publication, also includes positioning means for moving the static field magnet and the energy applicator to position the magnet and the applicator so that the magnetic resonance volume at least partially encompasses a region of the subject to be treated and so that the energy applicator is focused within the magnetic resonance volume. For example, the apparatus may include a chassis carrying both the static field magnet and the energy applicator, and the positioning means is arranged to move the chassis relative to the subject. The apparatus may further include ancillary equipment such as gradient coils mounted to the chassis or otherwise secured in position relative to the static field magnet for applying a magnetic field gradient within the magnetic resonance volume. Other ancillary equipment includes radio frequency equipment for applying radio frequency signals to the subject and receiving the resulting emitted radio frequency signals, hereafter referred to as magnetic resonance signals. Apparatus of this type may be used to acquire images of a region within the patient's body, and may also be used to perform therapeutic procedures such as thermal ablation of tumors or other undesired tissues. The therapeutic procedures can be monitored using the magnetic resonance apparatus. Combined magnetic resonance imaging and hyperthermia procedures can also be performed using conventional magnetic resonance imaging apparatus having a large, fixed static field magnet defining a patient-receiving space. In this case, the patient is disposed inside the patient-receiving space of the magnet, and the HIFU unit is positioned in or near this space.

In magnetic resonance imaging procedures, the region of the subject to be imaged is subjected to a strong magnetic field using the static field magnet. Radio frequency signals are applied to the tissues of the subject within the imaging volume. Under these conditions, atomic nuclei are excited by the applied radio frequency signals and emit faint radio frequency signals, referred to herein as magnetic resonance signals. By applying appropriate gradients in the magnetic field during the procedure, the magnetic resonance signals can be obtained selectively from a limited region such as a two-dimensional slice of the subject's tissue. The frequency and phase of the signals from different portions of the slice can be made to vary with position in the slice. By applying known techniques, it is possible to deconvolute the signals arising from different portions of the slice and to deduce certain properties of the tissues at each point within the slice from the signals. In some magnetic resonance procedures, these properties are determined for tissues at numerous closely-spaced locations so as to form an image of the subject, whereas in other magnetic resonance procedures, signals are acquired from one or more discrete locations within the subject, without developing an image of the subject.

A problem arises in procedures which employ an energy applicator such as a HIFU unit or other electrical apparatus in conjunction with the magnetic resonance procedures. Depending on its specific configuration, the electrical apparatus may emit unwanted radio waves, referred to herein as "RF noise". For example, a HIFU unit, as disclosed in the copending application, may emit RF noise when it generates its bursts of high intensity focused ultrasound. The RF noise can interfere with the magnetic resonance signal received by the radio frequency equipment.

SUMMARY OF THE INVENTION

One aspect of the present invention provides methods of performing magnetic resonance procedures while also using an electrical appliance. As used in this disclosure, the term "electrical appliance" should be understood as referring to any device which is supplied with electrical energy or which emits RF noise, but does not include a part of the magnet and RF transmitter and receiver used to create the magnetic resonance image. Thus, the term "electrical appliance" includes, without limitation, devices such as energy applicators including HIFU units and other ultrasonic emitters, electronic instruments such as cathode ray tubes, television equipment such as the television cameras incorporated in certain endoscopes, and the like. According to this aspect of the invention, the electrical appliance is activated only when the RF receiver of the magnetic resonance apparatus is not actively receiving a magnetic resonance signal. Stated another way, the electrical appliance is activated only while the RF receiver is inactive.

As further described below, magnetic resonance procedures include cycles of timed steps, commonly referred to as "pulse sequences". One of these steps includes receiving the magnetic resonance signals emitted by the subject. The signals typically are received only during predetermined periods, referred to herein as "receive intervals". This aspect of the invention incorporates the realization that the receive intervals occupy only a fraction of the total cycle time, and that RF noise emitted during other parts of the cycle time will not adversely affect the magnetic resonance examination procedure to the same degree as RF noise emitted during the receive intervals. Preferred methods according to this aspect of the invention incorporate the further realization that many electrical appliances used in medical procedures can be operated intermittently with little loss of performance. In particular, operation of appliances such as HIFU units and other devices which are used to heat tissues can be interrupted during the receive intervals and still can provide satisfactory performance. Thus, in methods according to this aspect of the invention, an electrical appliance separate from the magnetic resonance system is deactivated during the receive intervals and is activated only during intervals when the RF receiver is not collecting magnetic resonance signals.

Methods according to a further aspect of the invention incorporate the realization that the RF noise emitted by an intermittently-operated electrical appliance can be tolerated if the data collected during particular pulse sequences adversely affected by such RF noise is discarded. Typically, the pulse sequence is repeated cyclically, and the magnitude of one or more of the gradients is changed in each cycle. The magnetic resonance data collected during the whole procedure is a composite of the information collected during the various cycles. For example, where the data is used to generate an image, the image is calculated from the data collected during all of the various cycles. In preferred methods according to this aspect of the invention, operation of the appliance is coordinated with the pulse sequence cycles so that cycles of the pulse sequence which are affected by such operation can be identified. For example, the appliance may be actuated at predetermined times, and the cycles of the pulse sequence may also be applied at predetermined times. Alternatively, the appliance may be actuated at times which have no preset relation to the times of particular pulse sequence, and actuation of the appliance may be detected so that the time of such actuation can be compared to the times of particular pulse sequence cycles to determine which cycles overlap with the appliance actuation. The RF receiver and/or data collection apparatus may be disabled during these cycles, so that no data is collected during these cycles and the magnetic resonance signals elicited in these cycles is discarded. Alternatively or additionally, magnetic resonance data associated with those cycles is discarded. Preferably, those cycles are repeated at a time when the appliance is inactive.

A further aspect of the invention provides apparatus which incorporates a magnetic resonance system having an RF receiver and an electrical appliance which is not part of the magnetic resonance system. The apparatus desirably includes means for disabling the electrical appliance while the RF receiver is active. As further discussed below, where the magnetic resonance system is controlled by a computer, the disabling means can include the control computer of the magnetic resonance system. Alternatively, the apparatus may include means for coordinating operation of the appliance with the times of pulse sequences so that pulse sequence cycles affected by operation of the appliance can be identified. In this case, the apparatus desirably also includes means for disabling the RF receiver or means for discarding data collected during the affected cycles. The apparatus may also include means for actuating the magnetic resonance system to repeat the affected cycles.

DETAILED DESCRIPTION

Figure 1:
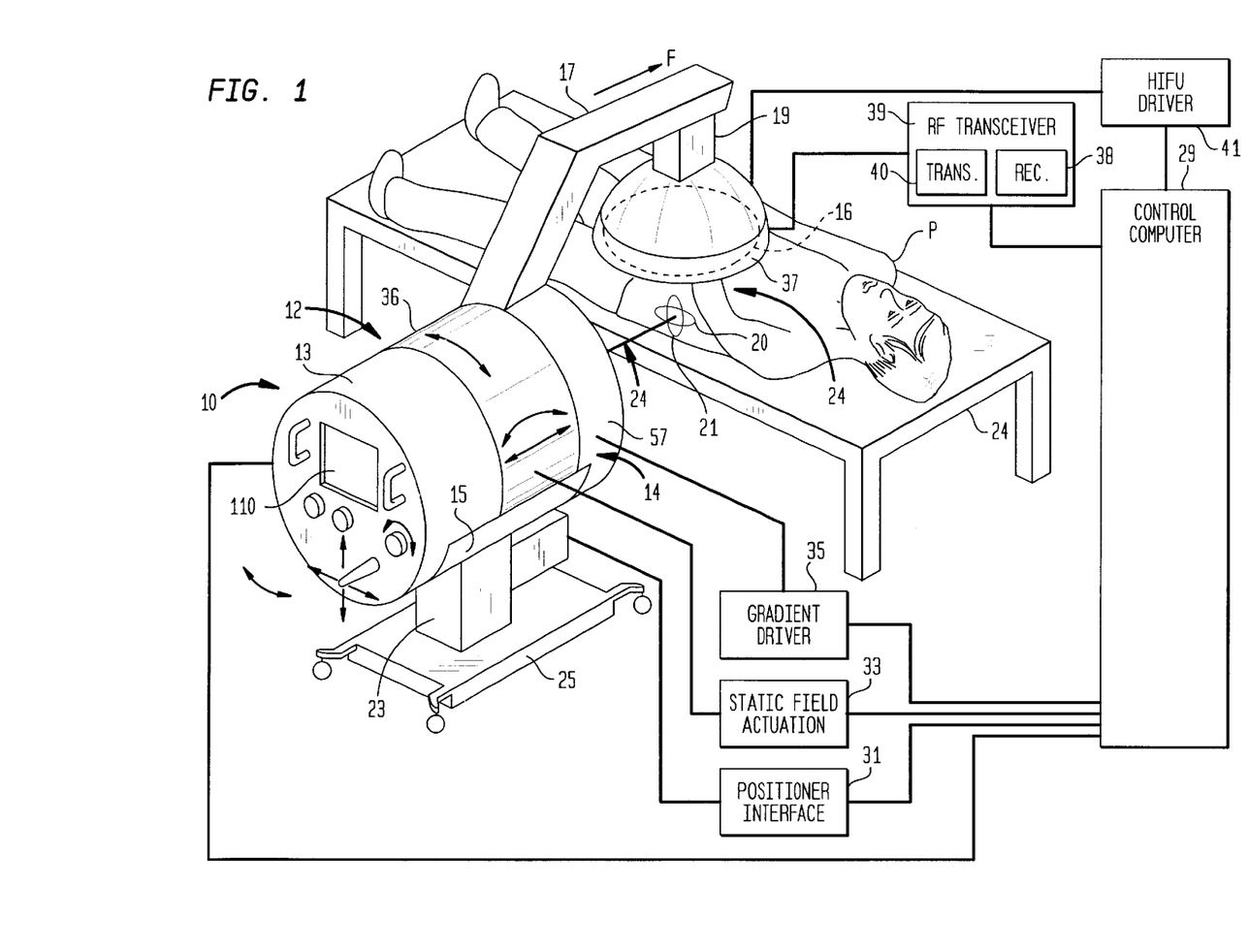
FIG. 1 is a perspective, partially block diagrammatic view depicting apparatus in accordance with one embodiment of the invention.

Apparatus in accordance with one embodiment of the invention includes a mobile unit 10 incorporating a static field magnet 12 and a gradient coil assembly 14 all mounted to a common chassis 15. The chassis 15 includes an arm 17 projecting upwardly from the other components and projecting in a forward direction indicated by arrow F in FIG. 1. A command and control console 13 is also included. A mounting socket 19 at the forward end of arm 17 carries a high-intensity focused ultrasound or "HIFU" emitter 16. The static field magnet 12 is arranged to provide a suitable magnetic field for magnetic resonance imaging within a magnetic resonance volume 20 disposed forwardly of unit 10, whereas the HIFU unit 16 is arranged to apply ultrasonic energy at selected focal points within an energy application zone 21 intersecting magnetic resonance volume 20. The particular magnet illustrated in FIG. 1 is a movable magnet. As described in greater detail in the '465 Publication, such a movable magnet can be moved to bring the magnetic resonance volume 20 into alignment with the desired region of the patient P. Thus, chassis 15 is mounted on a positioning system 23 which is linked to a control computer 29. In the particular structure depicted, the command and control console 13 is mounted on the chassis 15. However, the command and control console may be mounted remote from chassis 15, as, for example, outside of room where the magnet is housed. In this case, the chassis may be moved by remote control devices (not shown).

Control console 13 is also linked to control computer 29. The static field magnet 12 may be a superconducting magnet with one or more auxiliary shim coils activated by static field actuation unit 33, whereas a gradient driver 35 actuates the gradient coils 14 to impose magnetic field gradients as discussed below. A radio frequency antenna 37 is mounted around the HIFU unit 16 and linked to an RF transceiver 39. The transceiver 39 is also controlled by control computer 29. The transceiver includes a transmitter 38 and a receiver 40. Further, an electrical driver 41 is connected to HIFU unit 16. Driver 41 is also controlled by control computer 29. These components cooperate to perform magnetic resonance imaging within magnetic resonance volume 20 and to apply ultrasonic energy at selective points in energy application volume 21.

The physical structure of the HIFU unit and magnet can be varied from those shown in FIG. 1. For example, the static field magnet 12 and gradient coils 14 can be mounted on a moveable chassis disposed beneath the patient support bed 24, whereas the HIFU unit 16 may be mounted above the patient support bed, on a separate movable chassis or on an extension of the chassis which carries the static field magnet and gradient coils. Also, the HIFU unit can have any shape which provides the desired sonic properties. For example, the HIFU unit may include a flat array of transducers and a water-filled balloon. One such unit is described in detail in commonly assigned United States Provisional Patent Application No. 60/252,700, the disclosure of which is incorporated by reference herein.

RF transceiver 39 is connected to an antenna 37. The transceiver typically includes a relatively high powered transmitting section and a sensitive receiver, together with devices for disabling the receiver when the transmitter is actuated and vice versa. The RF antenna and transceiver are tunable to frequencies corresponding to the range of Larmor frequencies or magnetic resonance frequencies for protons subjected to the magnetic fields of the static field magnet. The foregoing elements of the apparatus may be generally in accordance with the '465 publication or of other known construction.

Figure 2:
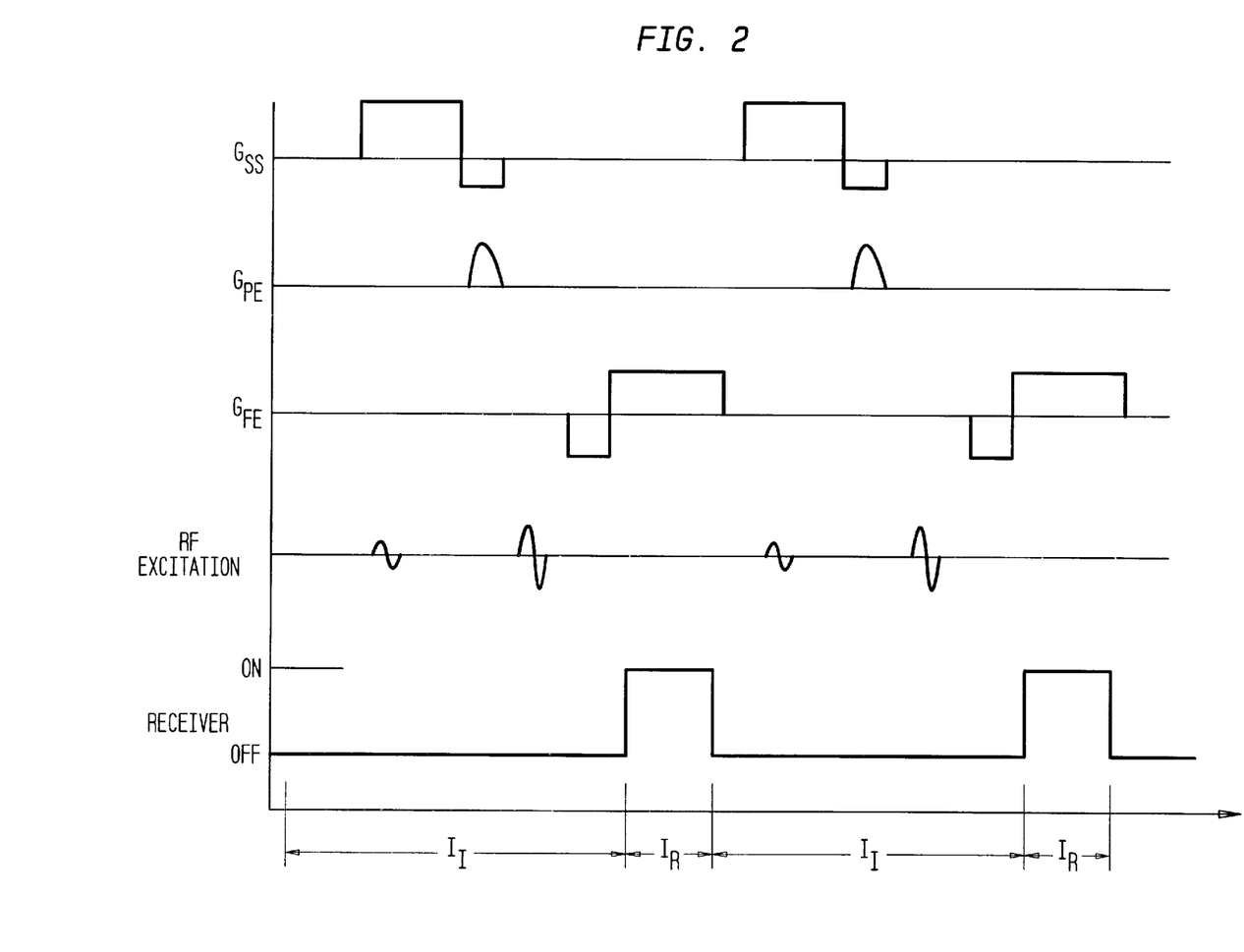
FIG. 2 is a schematic timing diagram for an MRI pulse sequence using the 'spin-echo' imaging process.

In performing a magnetic resonance imaging ("MRI") procedure and applying HIFU using the apparatus above, many different operations must take place in sequence. The exact nature and timing of the operations in an MRI scan can vary from scan to scan. One rudimentary MRI pulse sequence is depicted in FIG. 2. In the simplest mode of operation, a slice selection magnetic field gradient $G_{SS}$ is applied simultaneously with the application of an RF pulse from the transmitter. Then a phase encoding magnetic field gradient $G_{PE}$ is applied, and a further RF pulse is applied. Then a frequency encoding gradient $G_{FE}$ is applied while the magnetic resonance signal (an RF signal) is received during a receive interval $I_R$. This cycle of operations is repeated, and one or more of the gradients is varied during each repetition. The RF receiver 40 incorporated in transceiver 38 is activated only during the receive intervals, and is inactive at other times. Thus, during inactive intervals $I_I$, receiver 40 may be turned off or may be disconnected from antenna 37. Alternatively, if receiver 40 is arranged so that it can withstand high RF power input, the receiver may remain operational but the output signal from the receiver may be discarded. Any or all of these methods may be used to render the receiver inactive and incapable of receiving RF signals. Of course, the particular magnetic resonance imaging pulse sequence depicted in FIG. 2 is merely for purposes of illustration; as known to those skilled in the magnetic resonance imaging art, many different sequences of gradients, RF excitation pulses and receive intervals may be employed. Any of these known sequences can be employed in the present invention.

As described in further detail in the '465 publication, the HIFU unit can be actuated to provide hyperthermia as, for example, in surgical procedures where hyperthermia is used for ablation. Control computer 29 operates the HIFU driver so that the HIFU driver applies electrical signals to HIFU unit 16 only during the inactive intervals II, while the receiver 40 is inactive. As described in greater detail in the '465 publication, the control computer may be arranged to apply the ultrasonic energy in pulses; one or more pulses may be applied during each inactive interval $I_I$. In a variant of this approach, where the HIFU unit or other appliance is actuated manually, the control computer may be connected to the appliance so that the control computer can override a manually-input command to activate the appliance. In one simple system (FIG. 3), the control computer 229 is connected to a switch 201 in series with the manual activation control 203 of the appliance or in series with the power supply 207 to the appliance. Substantially the same control scheme can be applied to control other appliances used in proximity to the magnetic resonance apparatus. Typically, the magnetic resonance apparatus is operated within an RF-shielded enclosure to suppress ambient RF noise. The control scheme can be applied to control appliances used within the shielded enclosure.

Figure 3:
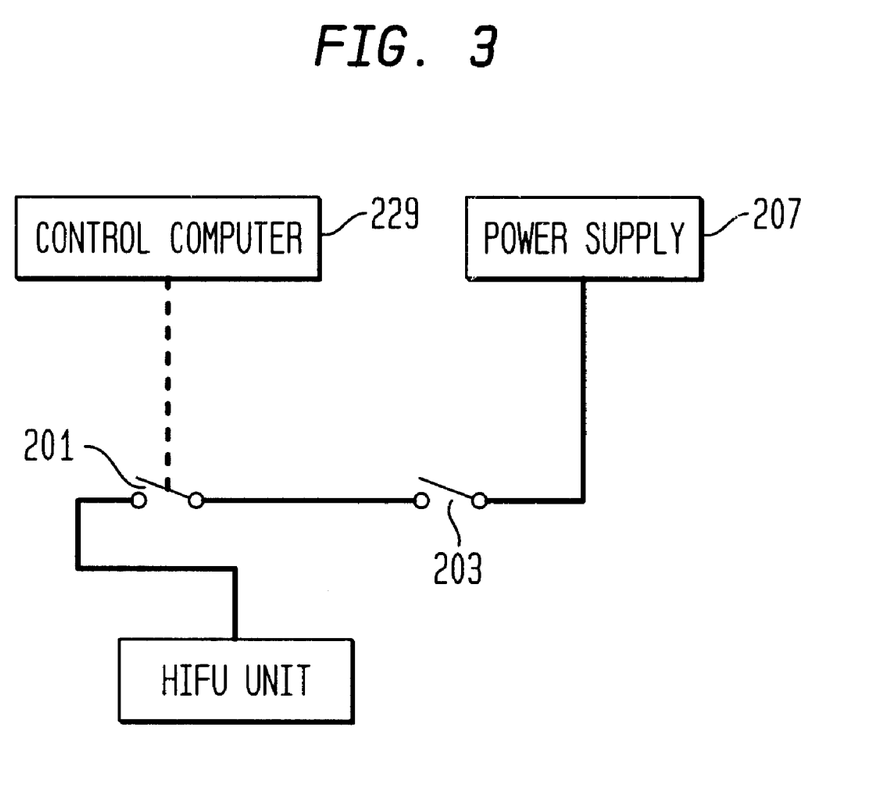
FIG. 3 is a partial block diagram of apparatus according to a further embodiment of the invention.

In the embodiment discussed above, the HIFU unit is deactivated directly by the control computer . In an alternative according to a further embodiment of the invention, the HIFU unit 16 or other appliance can be linked to the transceiver through an intermediate control circuit so that the appliance is shut off in response to activation of the receiver. The intermediate control circuit can override a manually-applied or computer-generated activation signal.

As discussed above, the frequency encoding gradient normally is applied to the subject during the receive intervals $I_R$ in typical magnetic resonance imaging sequences in order to obtain a magnetic resonance signal which is usable to construct an image. Therefore, another way to assure that the appliance is inactive during the receive intervals is to disable the appliance when the frequency encoding gradient is applied. For example, the HIFU unit 16 or other energy applicator can be set (through either the controlling software or hardwired intermediate control circuitry) such that no ultrasonic or other energy is emitted while this magnetic field gradient is active. This approach is less preferred because in some pulse sequences, the frequency encoding gradient is active at times other than during the receive intervals, and the appliance will be deactivated unnecessarily when such a pulse sequence is employed. However, this approach does ensure that the HIFU unit or other appliance is deactivated when the magnetic resonance signal is being received.

In the embodiments discussed above, the HIFU unit or other appliance may be activated during portions of a pulse sequence while the receiver is inactive. Although this arrangement produces much less interference with the received magnetic resonance signals than would occur upon operation of the HIFU unit simultaneously with the RF receiver, the interference may not be reduced to zero. Thus, some impairment of the image may still occur. Although the present invention is not limited by any theory of operation, it is believed that this minor impairment can arise when the RF noise emitted by the appliance excites an antenna of the magnetic resonance system at a resonant frequency corresponding to the Larmor frequency in the region to be imaged. The antenna radiates an extra excitation signal into the region of interest. To minimize this effect, the antenna system may be detuned automatically during actuation of the appliance.

The foregoing description refers to the appliance as being either actuated or inactive. In practice, the appliance emits RF noise during a "ringdown" interval following actuation, while the electrical currents in the appliance are decaying. The length of this "ringdown" interval will vary with the type of appliance; with the type of drive circuit used to actuate the appliance; and with the level of decay taken as the end of the ringdown interval. For a typical HIFU unit, the ringdown interval required for the emissions to decay to less than about 3% of their magnitude during actuation may be on the order of milliseconds. The appliance can be regarded as active during the ringdown interval.

Apparatus according to a further embodiment of the invention (FIG. 4) incorporates a magnet assembly 112 having a static field magnet and gradient coil similar to those discussed above, with associated static field actuation unit 133, gradient driver 135 and RF transceiver 139 similar to those discussed above. As in the embodiment discussed above, these components are linked to a control computer 129 which is arranged to operate these components cyclically so as to repeat the steps constituting a pulse sequence in a series of cycles at times set by the control computer. The control computer includes an internal memory 101 for storing data representing magnetic resonance signals received by transceiver 139, and further includes a program memory 103 for storing a program controlling the computer and a conventional timer such as the internal clock of the computer.

Figure 4:
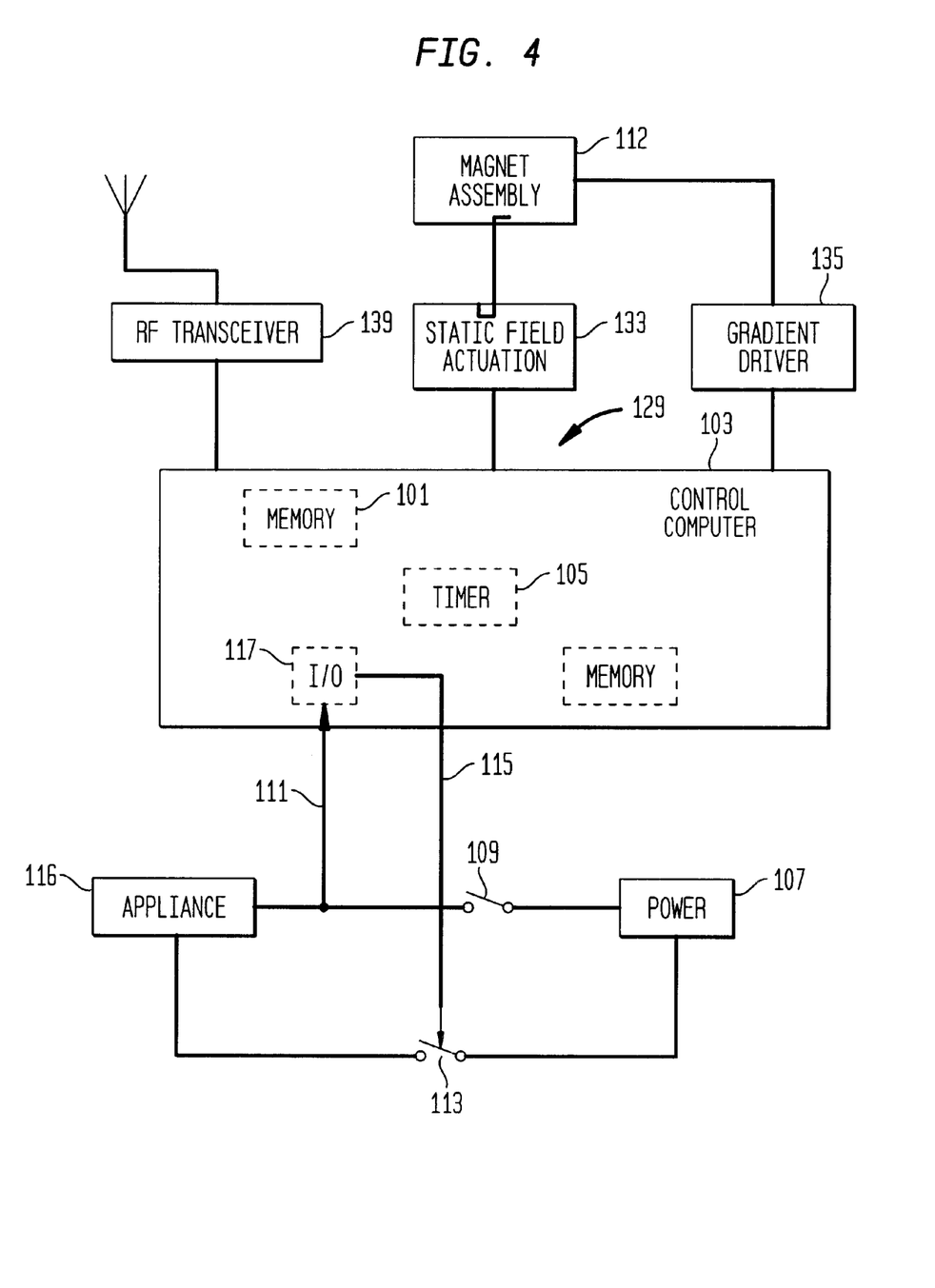
FIG. 4 is a block diagram depicting apparatus in accordance with another embodiment of the invention.

The system further includes an appliance 116, such as a HIFU unit or other electrically-actuated appliance. A power source 107 such as a power supply unit or a utility power outlet is connected to the appliance 116 through a manually-controlled switch 109. A power sense line 111 is connected to a node between switch 109 and appliance 116, so that sense line 111 will be energized when power is applied to the appliance through switch 109 and deenergize when switch 109 is open. A slave switch 113 is also connected between the power source 107 and appliance 116, so that power can be supplied to appliance 116 through slave switch 113. Slave switch 113 is controlled by a signal on a control line 115. Control line 115 and sense line 111 are connected to a conventional input/output interface unit 117 in control computer 129. These connections are arranged so that the computer receives one input signal when sense line 111 is energized and a different input signal when sense line 111 is not energized. Also, I/O unit 117 is arranged to translate a command within computer 129 into a control signal on control line 115 to open or close switch 113.

In a method according to a further embodiment of the invention, computer 129 commands the magnetic resonance components, including transceiver 139 and magnet assembly 112 to perform the RF excitation, gradient application and magnetic resonance signal reception steps constituting a pulse sequence in a series of cycles, at times set using timer 105. In the conventional manner, one or more of the field gradients applied during the pulse sequence is varied as discussed above so that such gradient has different magnitudes during different cycles. The control computer records the RF signals in memory 101. At some time during the process, the person operating the equipment manually actuates switch 109 and hence actuates appliance 116. Computer 129 receives an input signal denoting actuation of the appliance on line 111, and records the time of such actuation in memory 101. When actuation ceases, the computer receives another signal on line 111, and records the time of that signal in memory 101. The computer thus has information denoting the actuation interval of appliance 116. The computer compares that actuation interval with the times of the receive intervals of the various cycles and thus identifies those cycles in which the receive intervals overlap with the actuation interval. The computer commands memory 101 to erase the data representing magnetic resonance signals from the identified cycles so as to reject data acquired in these cycles, and commands the magnetic resonance components to repeat those cycles with the appropriate gradients and reacquire the data. The reacquired data is used in conjunction with the data from other cycles to form an image or provide other information about the patient or other subject. The repeat cycles may be performed at any time after the need for such repeat cycles has been determined as, for example at the end of the set of cycles or immediately after termination of the appliance actuation interval. In a variant of this approach, the computer can deactivate the receiver portion of transceiver 139, or disable storage of received data into memory 101, in response to the input signal denoting actuation of the appliance so as to reject the data. The computer can record the cycles where such deactivation occurs and repeat such cycles. In a less-preferred embodiment, the identified cycles may not be repeated; the image reconstruction or other information-deriving steps performed by the computer are performed without the data from the identified cycles.

In the methods according to this embodiment, slave switch 113 remains open and inactive. Thus, if the apparatus is to be used only in this way, the slave switch can be omitted. In a variant of this method, actuation of the appliance is detected by sensing its output, as, for example, by detecting RF noise using transceiver 139 or by detecting ultrasonic emissions from a HIFU appliance.

In a method according to a further embodiment of the invention, manual switch 109 is left open and inactive. Computer 129 actuates slave switch 113, and hence actuates appliance 116, at predetermined times corresponding to pre-selected cycles. The cycles overlapping with the appliance actuation are known from the pre-selected actuation times. In other respects, the method is similar to that described above. Methods as discussed with reference to FIG. 4 can be used, for example, to accommodate appliance actuation intervals longer than the inactive intervals discussed above with reference to FIG. 2.

Although the foregoing description of the preferred embodiments refers to systems using movable static field magnets, the invention can also be practiced with conventional fixed magnets such as fixed magnets having internal space for receiving the subject.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Apparatus for performing operations on a subject comprising:
    (a) a magnetic resonance system including a magnet and an RF transmitter for eliciting magnetic resonance signals from a subject and an RF receiver for receiving said magnetic resonance signals;
    (b) means for controlling operation of an electrical appliance which appliance is separate from said magnetic resonance system so that the appliance will not operate while the receiver is receiving the magnetic resonance signals.

2. Apparatus as claimed in claim 1 further comprising a control computer connected to said receiver, said control computer being operative to control said receiver so that said receiver is active only during receive intervals separated by inactive intervals, and wherein said means for controlling includes said control computer.

3. Apparatus as claimed in claim 1 wherein said control means includes an intermediate control circuit connected to said receiver.

4. Apparatus for performing operations on a subject comprising:
    (a) a magnetic resonance system including a magnet, an RF transmitter, an RF receiver for receiving said magnetic resonance signal and a control unit for actuating said magnet, transmitter and receiver to elicit magnetic resonance signals from a subject during a plurality of cycles;
    (b) an electrical appliance which is separate from said magnetic resonance system;
    (c) means for coordinating actuation of said appliance with said cycles so that the cycles during which said appliance is actuated can be identified; and
    (d) means for rejecting magnetic resonance signals elicited in at least some of the cycles during which said appliance is actuated.

5. Apparatus as claimed in claim 4 wherein said means for coordinating includes means for actuating said appliance at predetermined times having a preset temporal relation with said cycles.

6. Apparatus as claimed in claim 5 wherein said appliance is connected to said control device of said magnetic resonance system and said means for actuating at predetermined times includes said control device.

7. Apparatus as claimed in claim 4 wherein said means for coordinating includes means for detecting operation of said appliance and providing an actuation signal to said control device denoting the times of such actuation.

8. Apparatus as claimed in claim 4 wherein said means for rejecting includes means for inactivating said RF receiver in cycles during which said appliance is activated.

9. Apparatus as claimed in claim 4 wherein said means for rejecting includes means for discarding data obtained from cycles during which said appliance is activated.

10. A method of performing a procedure on a subject comprising the steps of:
  (a) eliciting magnetic resonance signals from the subject using a magnetic resonance system and receiving said magnetic resonance signals during receive intervals separated in time from one another by inactive intervals; and
  (b) actuating an electrical appliance separate from said magnetic resonance system only during said inactive intervals and deactivating said appliance during said receive intervals.

11. A method as claimed in claim 10 wherein said magnetic resonance apparatus and said appliance are controlled by a common control computer.

12. A method as claimed in claim 10 wherein said actuating and deactivating step includes deactivating said appliance responsive to actuation of said receiver.

13. A method as claimed in claim 10 wherein said step of eliciting magnetic resonance signals includes applying a frequency encoding gradient to the subject, said receiver being active only during application of said frequency encoding gradient, said activating and deactivating steps including, actuating the appliance only when the frequency encoding gradient is not applied.

14. A method as claimed in claim 10 wherein said appliance is operative to heat a region of the subject.

15. A method as claimed in claim 10 wherein said appliance is an ultrasonic energy applicator.

16. A method of performing a procedure on a subject comprising the steps of:
  (a) eliciting magnetic resonance signals from the subject using a magnetic resonance system and receiving said magnetic resonance signals in a series of cycles;
  (b) actuating an electrical appliance separate from said magnetic resonance system during one or more of said cycles;
  (c) coordinating actuation of said appliance with said cycles so that the cycles during which said appliance is actuated can be identified; and
  (d) rejecting magnetic resonance signals elicited in at least some of the cycles during which said appliance is actuated.

17. A method as claimed in claim 16 further comprising the step of repeating the cycles in which the magnetic resonance signals were rejected.

18. A method as claimed in claim 16 wherein said step of rejecting magnetic resonance signals includes the step of inactivating an RF receiver during cycles in which the appliance is activated.

19. A method as claimed in claim 16 wherein said step of rejecting magnetic resonance signals includes the step of discarding data representing magnetic resonance signals obtained during cycles in which the appliance is activated.

20. A method as claimed in claim 16 wherein said coordinating step includes actuating said appliance at predetermined times so that said appliance is actuated during predetermined ones of said cycles.

21. A method as claimed in claim 16 wherein said coordinating step includes detecting actuation of said appliance.

22. A method as claimed in claim 21 wherein said appliance is actuated by applying an input signal and said detecting step includes detecting said input signal.

23. A method as claimed in claim 21 wherein said detecting step includes detecting an effect caused by operation of said appliance.

24. A method as claimed in claim 23 wherein said effect includes RF signals emitted by said appliance and said detecting step is performed at least in part by using the same RF receiver as used to receive the magnetic resonance signals.

25. A method as claimed in claim 16 wherein said appliance is operative to heat a region of the subject.

26. A method as claimed in claim 16 wherein said appliance is an ultrasonic energy applicator.

* * * * *

UNITED STATES PATENT AND TRADEMARK OFFICE
CERTIFICATE OF CORRECTION

PATENT NO. : 6,501,978 B2
DATED : December 31, 2002
INVENTOR(S) : Mark Wagshul and Todd Fjield It is certified that error appears in the above-identified patent and that said Letters Patent is hereby corrected as shown below:

<u>Title page,</u>
Item [75], Inventors, "Shoreland" should read -- Shorham --.

Signed and Sealed this

Eighth Day of July, 2003

JAMES E. ROGAN
*Director of the United States Patent and Trademark Office*